United States Patent [19]

Larock

[11] 4,052,423

[45] Oct. 4, 1977

[54] SYNTHESIS OF α,β-UNSATURATED CARBOXYLIC ACIDS AND ESTERS

[75] Inventor: Richard Craig Larock, Ames, Iowa

[73] Assignee: Iowa State University Research Foundation, Inc., Ames, Iowa

[21] Appl. No.: 650,143

[22] Filed: Jan. 19, 1976

[51] Int. Cl.² .......................... C11C 3/02; C09F 5/08
[52] U.S. Cl. ........................ 260/410.9 R; 260/410; 260/413; 260/465.4; 260/515 R; 260/526 N; 260/514 M; 560/1; 560/8; 560/103; 560/205
[58] Field of Search ......... 260/515 R, 526 N, 468 M, 260/486 AC, 476 R, 410.9 R, 465.4, 469, 514 M, 410, 413

[56] References Cited

U.S. PATENT DOCUMENTS

| 3,316,290 | 4/1967 | Fenton | 260/486 AC |
|---|---|---|---|
| 3,427,344 | 2/1969 | Tsuji et al. | 260/486 AC |
| 3,527,794 | 9/1970 | Heck | 260/410.9 R |
| 3,668,249 | 6/1972 | Fenton | 260/410.9 R |
| 3,783,140 | 1/1974 | Heck | 260/515 R |
| 3,917,670 | 11/1975 | Baird et al. | 260/486 AC |

FOREIGN PATENT DOCUMENTS

| 1,164,561 | 9/1969 | United Kingdom | 260/410.9 R |
|---|---|---|---|

*Primary Examiner*—Patrick P. Garvin
*Assistant Examiner*—John F. Niebling
*Attorney, Agent, or Firm*—Zarley, McKee, Thomte, Voorhees & Sease

[57] ABSTRACT

α,β-Unsaturated carboxylic acids and esters have a wide variety of chemical uses. The invention is a method of synthesizing α,β-unsaturated carboxylic acids and esters which, with regard to the esters, comprises reacting a vinylmercuric halide with carbon monoxide in an alcohol to provide an α,β-unsaturated carboxylic acid ester. With regard to the acids per se, the method comprises reacting a vinylmercuric halide with carbon monoxide, in the presence of a water containing polar organic solvent to provide an α,β-unsaturated carboxylic acid.

14 Claims, No Drawings

SYNTHESIS OF α,β-UNSATURATED CARBOXYLIC ACIDS AND ESTERS

BACKGROUND OF THE INVENTION

α,β-unsaturated carboxylic acids and esters have the following basic formula:

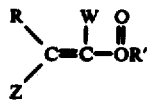

of course, with regard to the acids, R' represents hydrogen. Some of the multitude of uses for certain of these acids and esters includes monomers for the synthesis of substituted acrylic ester polymers or co-polymers. Polyacrylic acid is a useful soil conditioner. Methyl methacrylate is useful in the synthesis of polymeric thermoplastic solids and polymerizes to give a plastic called by its trade name Lucite. Many lacquers are derived from α,β-unsaturated esters. Many of the compounds are useful intermediates in the synthesis of other organic compounds. Sorbic acid, an α,β-unsaturated acid, inhibits the growth of fungi and molds and is useful as a food preservative. Compounds of the formula:

wherein R is hydrogen or alkyl as disclosed in U.S. Pat. No. 2,859,239, are useful perfume aromatics, insecticides, herbicides, parasiticides, bactericides, and fungicides. For further information with regard to α,β-unsaturated carboxylic acids and their esters and uses therefor see British Pat. No. 713,325, U.S. Pat. No. 2,807,633, French Pat. No. 952,985, British Pat. No. 668,530, U.S. Pat. No. 2,859,239, U.S. Pat. No. 2,883,418, British Pat. Nos. 779,277, 772,199, U.S. Pat. No. 2,849,466, French Pat. No. 1,413,529, U.S. Pat. No. 3,085,432, *Chemical Abstracts*, Vol. 76, 72151S (1972), *Chemical Abstracts*, Vol. 80, 23092X (1974), all of which are specifically incorporated herein by reference.

The wide range of usefulness of α,β-unsaturated carboxylic acids and their esters has stimulated efforts to provide economical means of synthesis of these compounds by simple synthetic routes providing the desired compounds in high yields.

It has now been found that a direct, simple, synthetic route yielding α,β-unsaturated carboxylic acids in high yields under a wide variety of reaction conditions can be achieved by utilizing vinylmercuric halides as a starting material in the reaction synthesis of α,β-unsaturated carboxylic acids and esters.

Accordingly, one object of this invention is to provide a general synthetic route which has universal application for the preparation of a wide variety of α,β-unsaturated carboxylic acids and esters.

Another object of this invention is to provide a synthetic method for α,β-unsaturated carboxylic acids and corresponding esters which involves only a single step synthesis and avoids the utilization of high temperatures and pressures often needed in prior art synthetic routes.

Yet another object of this invention is to provide a synthetic route for α,β-unsaturated carboxylic acids and esters which provides those compounds in unusually high yields when compared with prior art synthesis, generally yields in excess of 90% and often yields which are quantitative in nature.

Still another object of this invention is to provide α,β-unsaturated carboxylic acids and esters by a method which utilizes vinylmercuric halides as starting materials.

The method of accomplishing these and other objects of the invention will be apparent from the description of the invention which follows.

SUMMARY OF THE INVENTION

This invention relates to a method of preparing α,β-unsaturated carboxylic acids and esters. The method comprising reacting a vinylmercuric halide compound with carbon monoxide and alcohol to provide an α,β-unsaturated carboxylic acid ester. The reaction is preferably conducted in the presence of a noble metal catalyst. In the case of the preparation of α,β-unsaturated carboxylic acids per se, no alcohol is employed and the reaction is conducted in the presence of a water containing solvent, such as a 1 to 5% aqueous tetrahydrofuran solvent.

The reactions for synthesizing both the α,β-Unsaturated acids and the corresponding esters involve only a single-step synthesis utilizing the vinylmercuric halides as a starting material which provides the resulting desired product in yields in excess of 90% and often times quantitative.

DETAILED DESCRIPTION OF THE INVENTION

The reaction of this invention with regard to the preparation of α,β-unsaturated carboxylic acid esters may be summarized by the following equation:

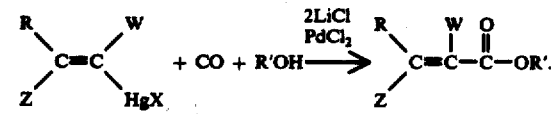

The reaction is substantially the same for the preparation of the acids except that no alcohol is employed and the reaction is conducted in the presence of a water-containing solvent. The preparation of the acids may be represented by the following general formula:

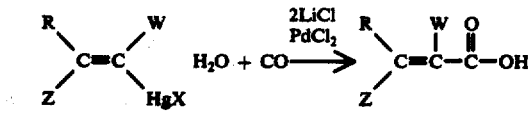

As can be seen for both general reactions set forth above, the starting material is a vinylmercuric halide wherein X represents any of the halide anions and may be chloride, bromide or iodide, for example. Vinylmercurials are readily available through acetylene addition reactions, see for example, R. C. Larock and H. C. Brown, *J. Organometal Chem.*, 36,1 (1972).

R. C. Larock, S. K. Guptal and H. C. Brown, *J. Amer. Chem. Soc.*, 94, 4371 (1972)

H. Staub, K. P. Zeller, and H. Leditschke, in Houben-Weyl's "Methoden der Organischen Chemie," Fourth ed., Vol. 13, G. Thieme Verlag, Stuttgart, 1974, Pt. 2b, pp. 192–199.

which are incorporated herein by reference.

Looking first at the reaction for the preparation of the α,β-unsaturated carboxylic acid esters, it can be seen that the reaction involves reacting a vinylmercuric halide with carbon monoxide and an alcohol to provide a direct carbonylation reaction. As previously mentioned with respect to the vinylmercuric halide, X represents the halide and may be chloride, bromide, iodide or the like. R, Z and W may be a wide variety of organic moieties or hydrogen, and are each preselected to represent moieties of the desired ester being synthesized. It is preferred, although not essential, that W represent hydrogen. It has been found that where W is not hydrogen there may be some sacrifice in yield. However, it should be understood that it is not critical, but only preferable for best yields that W represent hydrogen. Other compounds can be prepared wherein W does not represent hydrogen, with an attendant sacrifice in yield resulting.

It is preferred that R, W and Z, which represent moieties of the starting vinylmercuric halide, are selected from the group consisting of hydrogen, alkyl, aryl, substituted alkyls, substituted aryls, aralkyls, and substituted aralkyls. Most preferably, R is a lower $C_1$ to $C_8$ alkyl group, or phenyl, and Z and W are hydrogen.

R', which is the alkyl moiety of the alcohol utilized, is preferably a $C_1$ to $C_8$ alkyl and most preferably is methyl or ethyl.

As can be seen from the previously presented general reaction for the preparation of the α,β-unsaturated esters, the carbonylation reaction involves the removal of the mercuric halide moiety, HgX, from the vinylmercuric halide and the addition of the carbonyl group at the same situs, followed by an esterification reaction with the alcohol, providing the resulting α,β-unsaturated carboxylic acid ester. The carbonylation reaction is preferably conducted in the presence of either a reaction equivalent amount of a noble metal salt and lithium chloride or alternatively, and most preferably, is a palladium catalyst promoted carbonylation reaction conducted in the presence of a reoxidant such as cupric chloride. However, it is to be understood that other noble metals can be utilized with equally satisfactory results; for example, platinum, iridium, rhodium, ruthenium and the like. Where the noble metal salt promotion is utilized, lithium chloride is involved in an exchange reaction with the palladium salt. Where the noble metal catalyst is employed, the noble metal catalyst is either the noble metal on charcoal or a halide salt of a noble metal; for example, palladium chloride. Typically, in the catalytic promotion, about 1% by weight of the catalyst is employed and two equivalents of the cupric chloride reoxidant are employed to reoxidize the $Pd^\circ$ to $Pd^{2+}$. In summary, the carbonylation reaction is promoted by noble metals. Noble metal salts in combination with lithium chloride may be employed at reaction equivalent levels; or alternatively, catalytic amounts of the noble metal or its halide salts may be employed in the presence of a reoxidant such as cupric chloride.

There is no need to conduct the esterification reaction in the presence of any solvent since the alcohol employed functions as a solvent.

It is preferred that the carbonylation and the esterification reactions be conducted by adding the noble metal halide, the lithium chloride, and the alcohol together in a reaction flask. Thereafter, the reaction mixture may be cooled to temperatures as low as −78° C., and purged with carbon monoxide atmosphere. While purging with carbon monoxide is occurring, the vinylmercuric halide is added. After the entire amount of the vinylmercuric halide is added to the reaction mixture, the reaction mixture may then be gradually allowed to rise to room temperature. While low temperatures in the neighborhood of −20° to −78° C. can be utilized, temperatures as high as ambient temperatures may be employed. It therefore should be understood that temperature is not critical and that the reaction can equally as well be carried out under a variety of temperature conditions.

Because of the preference for obtaining high yield, it is preferred that reaction be conducted in the presence of one equivalent of palladium chloride and two equivalents of lithium chloride in order to give the highest yields. Although it should be understood that reaction may be conducted, if desired, in the presence of palladium chloride alone and in some cases yields as high as 85% of the ester have been obtained. The following table shows preparation of esters and the yields obtained by varying the amounts of palladium chloride and lithium chloride utilized:

Table I
Stoichiometry of Vinylmercuric Chloride Carboalkoxylation.

| Vinylmercuric Chloride | $PdCl_2$ (mmol) | LiCl (mmol) | Alcohol | Temp, °C | Ester Yield (%) |
|---|---|---|---|---|---|
| (phenyl-CH=CH-HgCl) | 0.5 | — | $CH_3OH$ | 0 | 85 |
|  | 0.5 | 1.0 |  |  | 95 |
|  | 1.0 | — |  |  | 87 |
|  | 1.0 | 2.0 |  |  | 100 |
| (n-$C_4H_9$-CH=CH-HgCl) |  |  | $C_2H_5OH$ |  | 88 |
|  |  |  | $CH_3OH$ |  | 88 |
|  |  |  |  | −20 | 95 |
|  |  |  |  | −78 | 99 |
|  |  |  | $C_2H_5OH$ | 0 | 67 |
|  |  |  |  | −20 | 95 |
|  |  |  |  | −78 | 95 |

The procedure employed in preparing the compounds set forth in Table I is the identical procedure disclosed in detail in Example 1 which follows.

As previously mentioned on several occasions, the method of this invention also finds applicability in the preparation of α,β-unsaturated carboxylic acids, as opposed to esters. The preparation of the acids is essentially the same as that previously described herein for the preparation of esters, except that no alcohol is employed. In other words, R' is hydrogen. The reaction is a direct carbonylation reaction which is conducted, of course, in the presence of water mixed in a water miscible organic solvent such as tetrahydrofuran. For the acid preparation, the reaction must be conducted at temperatures of 20° C. or lower, and the reaction is conducted in an aqueous, polar organic solvent system such as a mixture of water and acetone, ether, tetrahydrofuran, bis(dimethoxyethyl)ether, and the like. Preferably, the amount of water is from about 1 to about 10% by weight of the entire solvent system and most preferably is from about 1 to about 5% by weight of the solvent system. The most satisfactory solvent system for the preparation of the α,β-unsaturated acids has been found to be from about 1% to about 5% of water with tetrahydrofuran. Table II shows the preparation of a variety of α,β-unsaturated carboxylic acids utilizing aqueous tetrahydrofuran solvent systems employing various percent by weight amounts of water in the solvent system.

Table II
Preparation of α,β-Unsaturated Carboxylic Acids.

| Vinylmercuric Chloride | % Aqueous THF | Carboxylic Acid | % Isolated Yield |
|---|---|---|---|
| n-C$_4$H$_9$ / H / H / HgCl | 5 / 2 | n-C$_4$H$_9$ / H / H / COOH | 98 / 99 |
| (CH$_3$)$_3$C / H / H / HgCl | 5 | (CH$_3$)$_3$C / H / H / COOH | 98 |
| C$_6$H$_{11}$ / H / H / HgCl | 5 / 2 / 1 / 0.5 | C$_6$H$_{11}$ / H / H / COOH | 65 / 82 / 90 / 77 |
| C$_6$H$_5$ / H / H / HgCl | 5 / 1 | C$_6$H$_5$ / H / H / COOH | 80 / 30 |
| C$_2$H$_5$ / C$_2$H$_5$ / H / HgCl | 5 / 2 | C$_2$H$_5$ / C$_2$H$_5$ / H / COOH | 85 / 60 |
| NC(CH$_2$)$_3$ / H / H / HgCl | 5 / 2 | NC(CH$_2$)$_3$ / H / H / COOH | 72 / 65 |
| C$_6$H$_{11}$ / H / H / HgCl | 5 / 2 / 1 | C$_6$H$_{11}$ / H / H / COOH | 45 / 72 / 57 |

The method of preparation of the acids shown in Table II is exactly as described in Example 14 which follows hereinafter.

The following examples, as well as the examples listed in Tables I and II hereinbefore, are offered to further illustrate but not limit the invention disclosed herein.

EXAMPLE 1

(Preparation of methyl trans-β-cyclohexylacrylate)

Anhydrous lithium chloride (20 mmol), palladium chloride (10 mmol) and 100 ml methanol were added to a well-dried 250 ml round bottom flask containing a septum inlet and a carbon monoxide inlet tube. The flask was cooled to −78° C. and trans-cyclohexylethenylmercuric chloride (10 mmol) was added. The flask was flushed thoroughly with carbon monoxide along with continuous stirring. The reaction mixture was then allowed to slowly warm to room temperature over a 24-hour period, with continuous stirring, while maintaining a slight positive pressure of carbon monoxide.

Ether and activated carbon were added to the reaction mixture the next morning, and the mixture was filtered, washed with saturated ammonium chloride, and dried over anhydrous sodium sulfate. Removal of the solvent provided 1.61 g (96% of theoretical yield) of essentially pure methyl trans-β-cyclohexylacrylate. The presence of the essentially pure ester was confirmed by instrumental analysis, including infrared analysis, melting point analysis, molecular weight determinations, and other conventional instrumental techniques.

The following compounds were prepared in a similar fashion:

Methyl trans-2-undecenoate
Methyl trans-6-cyano-2-hexenoate
Methyl 2-dodecenedioate
Methyl α,-phenylcinnamate, mp 77° (lit mp 77°)

In addition, methyl cinnamate and methyl trans-2-heptenoate were prepared utilizing catalytic esterification reactions which employed vinylmercuric chloride (1 mmol), methyl alcohol (10 ml), anhydrous cupric chloride (2 mmol), anhydrous lithium chloride (2 mmol); and in the case of methyl cinnamate, 10% palladium on charcoal (0.1 mmol); and in the case of methyl trans-2-heptenoate, palladium chloride (0.1 mmol). The methyl cinnamate was prepared at 0° C., and the methyl trans-2-heptenoate at −78° C.

EXAMPLES 2 - 13

Carboxylic acid esters disclosed in the following table showing Examples 2 through 13 were prepared utilizing the vinyl-mercuric chloride compound listed and the alcohol listed, with the resulting listed yields. The manner of conducting the reactions was identical with that presented herein in Example 1.

Table III
Preparation of α,β-Unsaturated Carboxylic Esters

| Example | Vinylmercuric Chloride | Alcohol | Carboxylic Ester | % Isolated Yield |
|---|---|---|---|---|
| 2 | C$_6$H$_5$ / H / H / HgCl | CH$_3$OH | C$_6$H$_5$ / H / H / CO$_2$CH$_3$ | 100 |
| 3 | | C$_2$H$_5$OH | C$_6$H$_5$ / H / H / CO$_2$C$_2$H$_5$ | 99 |
| 4 | n-C$_4$H$_9$ / H / H / HgCl | CH$_3$OH | n-C$_4$H$_9$ / H / H / CO$_2$CH$_3$ | 98 |

Table III-continued

Preparation of α,β-Unsaturated Carboxylic Esters

| Example | Vinylmercuric Chloride | Alcohol | Carboxylic Ester | % Isolated Yield |
|---|---|---|---|---|
| 5 |  | $C_2H_5OH$ | n-$C_4H_9$\C=C/H, H/ \$CO_2C_2H_5$ | 93 |
| 6 | $(CH_3)_3C$\C=C/H, H/ \HgCl | $C_2H_5OH$ | $(CH_3)_3C$\C=C/H, H/ \$CO_2C_2H_5$ | 90 |
| 7 | n-$C_8H_{17}$\C=C/H, H/ \HgCl | $CH_3OH$ | n-$C_8H_{17}$\C=C/H, H/ \$CO_2CH_3$ | 98 |
| 8 | cyclohexyl\C=C/H, H/ \HgCl | $CH_3OH$ | cyclohexyl\C=C/H, H/ \$CO_2CH_3$ | 96 |
| 9 | $NC(CH_2)_3$\C=C/H, H/ \HgCl | $CH_3OH$ | $NC(CH_2)_3$\C=C/H, H/ \$CO_2CH_3$ | 98 |
| 10 | $CH_3O_2C(CH_2)_8$\C=C/H, H/ \HgCl | $CH_3OH$ | $CH_3O_2C(CH_2)_8$\C=C/H, H/ \$CO_2CH_3$ | 98 |
| 11 | H\C=C/$CH_3$, then /C=C\ H/ \HgCl | $C_2H_5OH$ | H\C=C/$CH_3$, then /C=C\ H/ \$CO_2C_2H_5$ | 93 |
| 12 | $C_2H_5$\C=C/$C_2H_5$, H/ \HgCl | $C_2H_5OH$ | $C_2H_5$\C=C/$C_2H_5$, H/ \$CO_2C_2H_5$ | 85 |
| 13 | (Ph)(Ph)C=C(H)(HgCl) | $CH_3OH$ | (Ph)(Ph)C=C(H)($CO_2CH_3$) | 99 |

EXAMPLE 14

(Preparation of 4,4-dimethyl-trans-2-pentenoic acid)

Anhydrous lithium chloride (20 mmol), palladium chloride (10 mmol), 5 ml of water and 95 ml of tetrahydrofuran were added to a 250 ml round bottom flask containing a septum inlet and carbon monoxide inlet tube (a balloon will suffice). The flask was cooled to −78° and 3,3-dimethyl-trans-1-butenylmercuric chloride (10 mmol) was added. The flask was thoroughly flushed with carbon monoxide. The well stirred reaction mixture was then allowed to slowly warm to room temperature over a 24 hour period and stirred overnight while maintaining a slight positive pressure of carbon monoxide. Ether and activated carbon were added to the reaction mixture which was filtered, washed with saturated ammonium chloride and finally extracted several times with saturated sodium bicarbonate solution. The bicarbonate solution was acidified with cold hydrochloric acid and extracted several times with ether. After drying over anhydrous $Na_2SO_4$ and removal of the solvent, 1.25 grams (98%) of essentially pure acid, mp 62°-62.5° (lit mp 61°-62°) is obtained.

The following α,β-unsaturated carboxylic acids were obtained in a similar manner. Trans-β cyclohexylacrylic acid, mp 57° (hexane) (lit. mp 57°-58°). Cinnamic acid, mp 132° ($H_2O$) (lit mp 132.6°-132.8°); Trans-6-cyano-2-hexenoic acid, mp 69.5°-70°; Trans-β-(1-cyclohexenyl) acrylic acid, mp 116.5°-117.5°.

I claim:

1. A method of preparing alpha beta-unsaturated carboxylic acid esters, said method comprising:

reacting in a Polar Solvent a vinylmercuric halide compound of the formula:

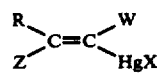

in the presence of a noble metal carbonylation promoter selected from the group consisting of reaction equivalent amounts of noble metal simple salts in combination with lithium chloride, catalytic amounts of noble metals, and noble metal halide simple salts with carbon monoxide and an alcohol of the formula R′OH to provide an alpha beta-unsaturated carboxylic acid ester of the formula:

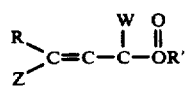

at a percentage of theoretical yield of at least 85 weight %, wherein R, Z, W and R′ are hydrogen or organic moieties which are non-reactive in the carbonylation reaction which occurs between said carbon monoxide and said vinylmercuric halide, of preselected determination to represent the desired ester being synthesized, and X is a halide.

2. The method of claim 1 wherein said catalyst is a palladium catalyst.

3. The method of claim 1 wherein said vinylmercuric halide is chloride.

4. The method of claim 1 wherein said reaction is conducted at a temperature of 0° C., or lower.

5. The reaction of claim 1 wherein Z and W are hydrogen.

6. The reaction of claim 5 where R and R' are selected from the group consisting of alkyl, aryl, substituted alkyls, substituted aryls, aralkyls, and substituted aralkyls.

7. The reaction of claim 5 wherein R is a lower, $C_1$ to $C_8$ alkyl group.

8. The reaction of claim 5 wherein R is a phenyl group.

9. The reaction of claim 5 wherein R' is a lower, $C_1$ to $C_8$ alkyl group.

10. The method of making alpha beta-unsaturated carboxylic acids, said method comprising;

reacting a vinylmercuric halide compound of the formula:

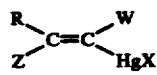

with carbon monoxide in the presence of water and a water miscible polar organic solvent and a noble metal carbonylation promoter selected from the group consisting of reaction equivalent amounts of noble metal simple salts in combination with lithium chloride, catalytic amounts of noble metals, and noble metal halide simple salts, the amount of said water being from about 1% by weight to about 10% by weight of the total amount of solvent present, said reaction being conducted at 20° C. or lower, to provide an alpha beta-unsaturated carboxylic acid of the formula:

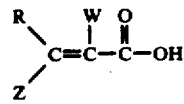

wherein R, Z and W are hydrogen or organic moieties which are non-reactive in the carbonylation reaction which occurs between said carbon monoxide and said vinyl mercuric halide, of pre-selected determination to represent the desired acid being synthesized, and X is the halide.

11. The method of claim 10 wherein said solvent is aqueous tetrahydrofuran.

12. The method of claim 11 wherein said tetrahydrofuran contains from about 1 to about 10% by weight of water.

13. The method of claim 12 wherein said tetrahydrofuran contains from about 1 to about 5% by weight of water.

14. A method of preparing alpha beta-unsaturated carboxylic acid esters, said method comprising: reacting in a Polar Solvent a vinylmercuric halide compound of the formula:

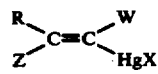

in the presence of a noble metal carbonylation promoter selected from the group consisting of reaction equivalent amounts of noble metal simple salts in combination with lithium chloride, catalytic amounts of noble metals, and noble metal halide simple salts with carbon monoxide and an alcohol of the formula R'OH to provide an alpha beta-unsaturated carboxylic acid ester of the formula:

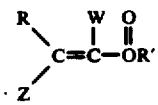

wherein R, Z, W and R' are moieties which are non-reactive in the carbonylation reaction which occurs between said carbon monoxide and said vinylmercuric halide of preselected determination to represent the desired ester being synthesized, and X is a halide.

* * * * *